(12) United States Patent
Kuroda et al.

(10) Patent No.: US 8,173,858 B2
(45) Date of Patent: May 8, 2012

(54) ABSORPTIVE ARTICLE AND METHOD OF PRODUCING THE SAME

(75) Inventors: Kenichiro Kuroda, Kagawa (JP); Yuki Noda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 391 days.

(21) Appl. No.: 12/515,850

(22) PCT Filed: Nov. 22, 2007

(86) PCT No.: PCT/JP2007/072672
§ 371 (c)(1),
(2), (4) Date: May 21, 2009

(87) PCT Pub. No.: WO2008/062873
PCT Pub. Date: May 29, 2008

(65) Prior Publication Data
US 2010/0057031 A1 Mar. 4, 2010

(30) Foreign Application Priority Data
Nov. 22, 2006 (JP) ................................ 2006-316348

(51) Int. Cl.
*A61F 13/15* (2006.01)
(52) U.S. Cl. ................. 604/378; 604/380; 604/385.101; 604/383
(58) Field of Classification Search .................. 604/378, 604/380, 385.101, 383
See application file for complete search history.

(56) References Cited

U.S. PATENT DOCUMENTS

| 4,568,341 | A | * | 2/1986 | Mitchell et al. | ............... | 604/368 |
| 5,030,229 | A | * | 7/1991 | Yang | ........................ | 604/385.05 |
| 2003/0119400 | A1 | | 6/2003 | Beitz et al. | | |

(Continued)

FOREIGN PATENT DOCUMENTS

EP 1568340 A1 8/2005

(Continued)

OTHER PUBLICATIONS

International Search Report of Application No. PCT/JP2007/072672 mailed Feb. 13, 2008.

(Continued)

*Primary Examiner* — Jacqueline F. Stephens
(74) *Attorney, Agent, or Firm* — Lowe, Hauptman, Ham & Berner, LLP

(57) ABSTRACT

An absorptive article in which an absorptive body is deformed into a stable recessed shape to prevent leakage of a large amount of discharged bodily wastes including bodily fluid. The absorptive article has a front side sheet at least a portion of which is liquid permeable and that is placed on the skin contact surface side, a liquid non-permeable back side sheet placed on the clothing contact surface side, and a liquid retainable absorptive body placed between the front side sheet and the back side sheet. The absorptive body has a compression section formed, when compressed from the clothing contact surface side to the skin contact surface side, into a projected shape projected on the clothing contact surface side, toward the skin contact surface side, and the absorptive body also has a space section formed, when compressed from the skin contact surface side to the clothing contact surface side, into a recessed shape recessed on the skin contact surface side, toward the clothing contact surface side. The space section is formed on each of both sides of or on one side of a projection section located on the opposite side of the compression section on the skin contact surface side.

15 Claims, 15 Drawing Sheets

U.S. PATENT DOCUMENTS

| | | |
|---|---|---|
| 2004/0176734 A1 | 9/2004 | Rasmussen et al. |
| 2004/0204698 A1 | 10/2004 | Zenker et al. |
| 2004/0243082 A1 | 12/2004 | Kinoshita et al. |
| 2004/0254554 A1 | 12/2004 | Mavinkurve et al. |

FOREIGN PATENT DOCUMENTS

| | | |
|---|---|---|
| JP | 10-099372 A | 4/1998 |
| JP | 2004528106 A | 9/2004 |
| JP | 2005512683 A | 5/2005 |
| JP | 2006-068551 A | 3/2006 |
| JP | 2007-319543 A | 12/2007 |
| JP | 2008-006266 A | 1/2008 |
| JP | 2008-006270 A | 1/2008 |
| JP | 2008-125917 A | 6/2008 |
| JP | 2008-125918 A | 6/2008 |
| WO | 02087484 A1 | 11/2002 |
| WO | 2006/130646 A1 | 12/2006 |

OTHER PUBLICATIONS

European Search Report issued to EP Application No. 07832401.9, mailed Nov. 28, 2011.

* cited by examiner

ABSORPTIVE ARTICLE AND METHOD OF PRODUCING THE SAME

RELATED APPLICATIONS

The present application is based on International Application Number PCT/JP2007/072672 filed Nov. 22, 2007, and claims priority from Japanese Application Number 2006-316348, filed Nov. 22, 2006, the disclosures of which are hereby incorporated by reference herein in their entirety.

TECHNICAL FIELD

The present invention relates to an absorbent article and a manufacturing method thereof. The present invention particularly relates to an absorbent article having superior leakproof properties and a manufacturing method thereof.

BACKGROUND ART

Sanitary napkins, panty liners, urine-absorbing pads and the like have conventionally been known as absorbent articles for absorbing discharged matter such as bodily fluid. These absorbent articles include an absorbent core for absorbing and holding bodily fluid or the like, a liquid permeable top sheet that is disposed on a skin contacting side of the absorbent article, and a liquid impermeable back sheet that is disposed on a clothing contacting side of the absorbent article. For example, these absorbent articles can be used in a state of being adhered to the internal surface of underwear.

In order to reliably trap the discharged matter discharged from an excretory part of a wearer, it is desired that such absorbent articles be used in a state where an absorbing portion of the absorbent core adheres to the excretory part. If there is a space between the excretory part and the absorbing portion, the discharged matter dropped on the top sheet may effuse along the top sheet toward sides of the absorbent article and the buttocks, resulting in leakage and soiling of the underwear and clothing.

However, in a case where the absorbing portion of the absorbent articles adheres to the excretory part of a wearer while wearing, for example, if a large amount of bodily fluid and the like is discharged at once, the discharged matter may effuse toward sides of the absorbent article and buttocks before being absorbed by the absorbent core, thereby causing leakage. In addition, for example, since the absorptive portion adheres to the excretory part of a wearer, the discharged matter such as bodily fluid and the like may come into direct contact with a wearer's skin before being absorbed, whereby comfort is diminished.

In contrast, Japanese Unexamined Patent Application Publication No. Hei 10-99372 (hereinafter referred to as Patent Document 1) discloses an absorbent article that can be used in a state of being deformed into a desired shape under a compressing force from a wearer's thigh, by way of grooves formed by a first flexible shaft and a second flexible shaft that are embossed from the skin contacting side and the clothing contacting side respectively, on a reverse side of a side being embossed.

DISCLOSURE OF THE INVENTION

Problems to be Solved by the Invention

However, in the sanitary napkin disclosed in Patent Document 1, since the second flexible shaft is provided in a region closer to the clothing contacting side than to the skin contacting side of the absorbent core, and thus a force applied from the second flexible shaft under a compressive force from the wearer's thigh in a width direction is dispersed to various directions, for example, toward the skin contacting side and toward the clothing contacting side in a thickness direction of the absorbent article. Therefore, the desired deformation cannot be maintained in the absorbent core. Consequently, in a case where a large amount of discharged matter such as bodily fluid is discharged, the absorbent article cannot sufficiently trap the discharged matter and may cause leakage.

The present invention has been made in view of the foregoing problems, and aims at providing an absorbent article that prevents leakage of discharged matter by retaining concave deformation of the absorbent core, thereby trapping a large amount of discharged matter.

Means for Solving the Problems

To this end, the present inventors have achieved the present invention based on the discovery that the absorbent core can be effectively deformed into a concave shape by providing predetermined compressed grooves on a clothing contacting side of the absorbent core and projecting a reverse side (skin contacting side) of the compressed grooves more to the skin contacting side than the skin contacting side of the absorbent core. More specifically, the present invention provides the following absorbent article.

In a first aspect of the present invention, an absorbent article includes: a top sheet that is at least partially liquid permeable and disposed on a skin contacting side; a back sheet that is liquid impermeable and disposed on a clothing contacting side; and an absorbent core that is liquid retentive and disposed between the top sheet and the back sheet, in which the absorbent core includes a compressed portion that is formed on the clothing contacting side in a convex shape toward the skin contacting side by compression from the clothing contacting side to the skin contacting side and a break portion that is formed on the skin contacting side in a concave shape toward the clothing contacting side by compression from the skin contacting side to the clothing contacting side, and in which the break portion is formed at least on one side of a projecting portion on a skin contacting side, which is on a reverse side of the compressed portion.

According to a second aspect of the present invention, in the absorbent article as described in the first aspect, the absorbent core includes a central core portion substantially in a center thereof, and the break portion is formed at least on a central core portion side of the projecting portion among both sides of the projecting portion.

According to a third aspect of the present invention, in the absorbent article as described in the second aspect, the absorbent core pushes down at least a part of the central core portion from the skin contacting side toward the clothing contacting side, by the projecting portion entering the break portion.

In a fourth aspect of the present invention, a manufacturing equipment of the absorbent article as described in any one of the first to the third aspects, includes a compressing portion forming device for forming the break portion that is formed in a concave shape on the skin contacting side and the compressed portion that is formed in a convex shape on the clothing contacting side by compressing the absorbent core from the skin contacting side and the clothing contacting side, in which the compressed portion forming device includes an upper die roller portion having a concave portion formed on a surface thereof in a predetermined pattern and a bottom die roller portion having a convex portion on a surface thereof that can removably fit into the concave portion, and in which the manufacturing equipment of the absorbent article forms the compressed portion and the break portion by compressing the absorbent core by way of the upper die roller portion and the bottom die roller portion, in a state where at least the absorbent core is tucked therebetween.

In a fifth aspect of the present invention, a manufacturing method of the absorbent article as described in any one of the first to the third aspects includes a compressing portion forming step of forming the break portion that is formed in a concave shape on the skin contacting side and the compressed portion that is formed in a convex shape on the clothing contacting side by compressing the absorbent core from the skin contacting side and the clothing contacting side, in which the compressing portion forming step uses an upper die roller portion having a concave portion formed on a surface thereof in a predetermined pattern and a bottom die roller portion having a convex portion on a surface thereof that can removably fit into the concave portion, and in which the manufacturing method of the absorbent article forms the compressed portion and the break portion by compressing the absorbent core by way of the upper die roller portion and the bottom die roller portion, in a state where at least the absorbent core is tucked therebetween.

EFFECTS OF THE INVENTION

According to the present invention, it is possible to provide an absorbent article capable of preventing the leakage of discharged matter by trapping the discharged matter that is discharged.

PREFERRED MODE FOR CARRYING OUT THE INVENTION

Embodiments of the present invention are described hereinafter with reference to the accompanying drawings. It is to be understood that the embodiments of the present invention are not limited thereto, and the technical scope of the present invention is not limited thereto. In the following description, one of the two surfaces of the absorbent article which is directed to the excretory part is called a "skin contacting side" and the other is called a "clothing contacting side", irrespective of whether or not clothing is worn on the outside thereof.

Figure 1:
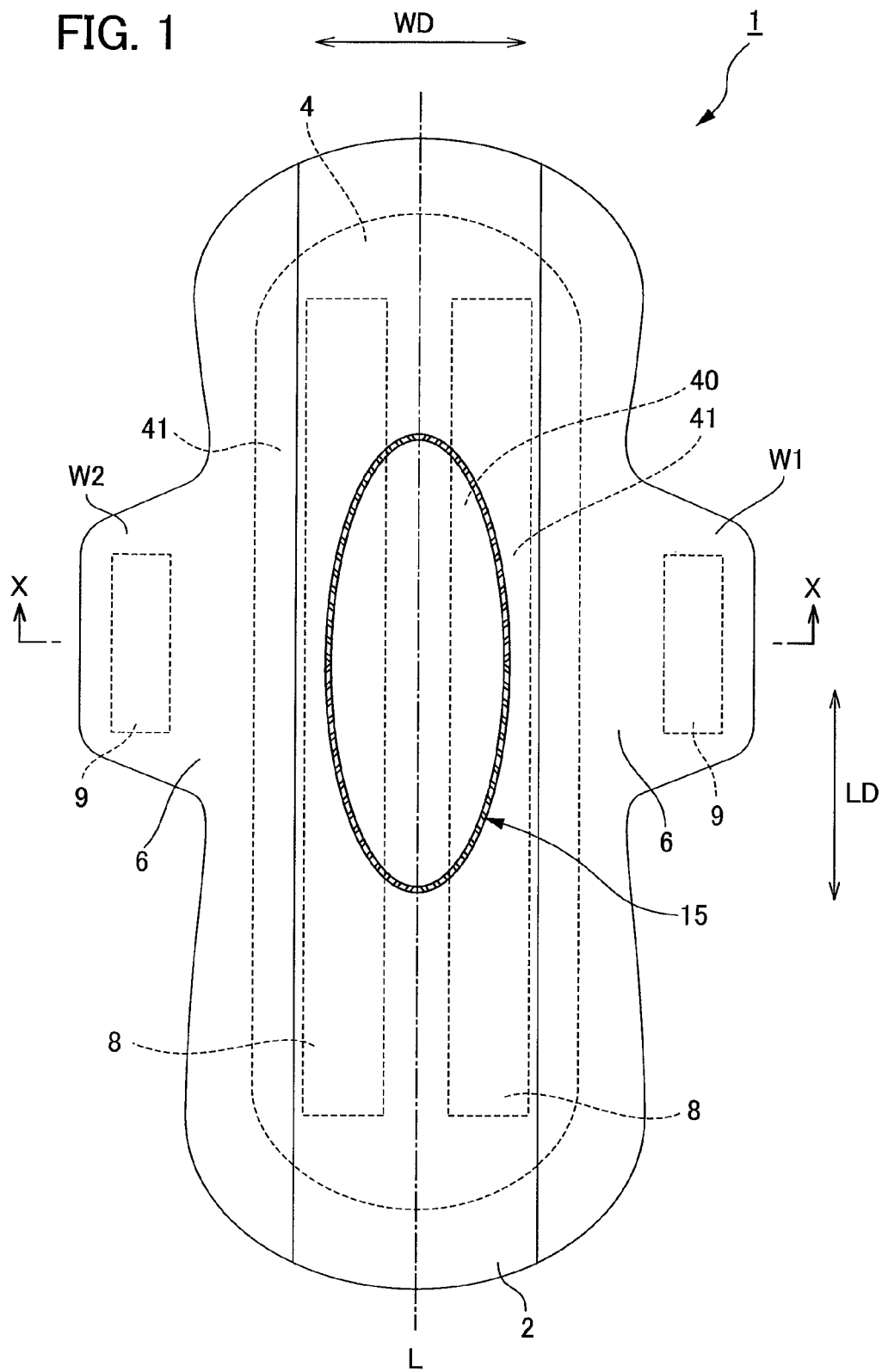
FIG. 1 is a plan view of a sanitary napkin according to a first embodiment of the present invention.
Figure 2:
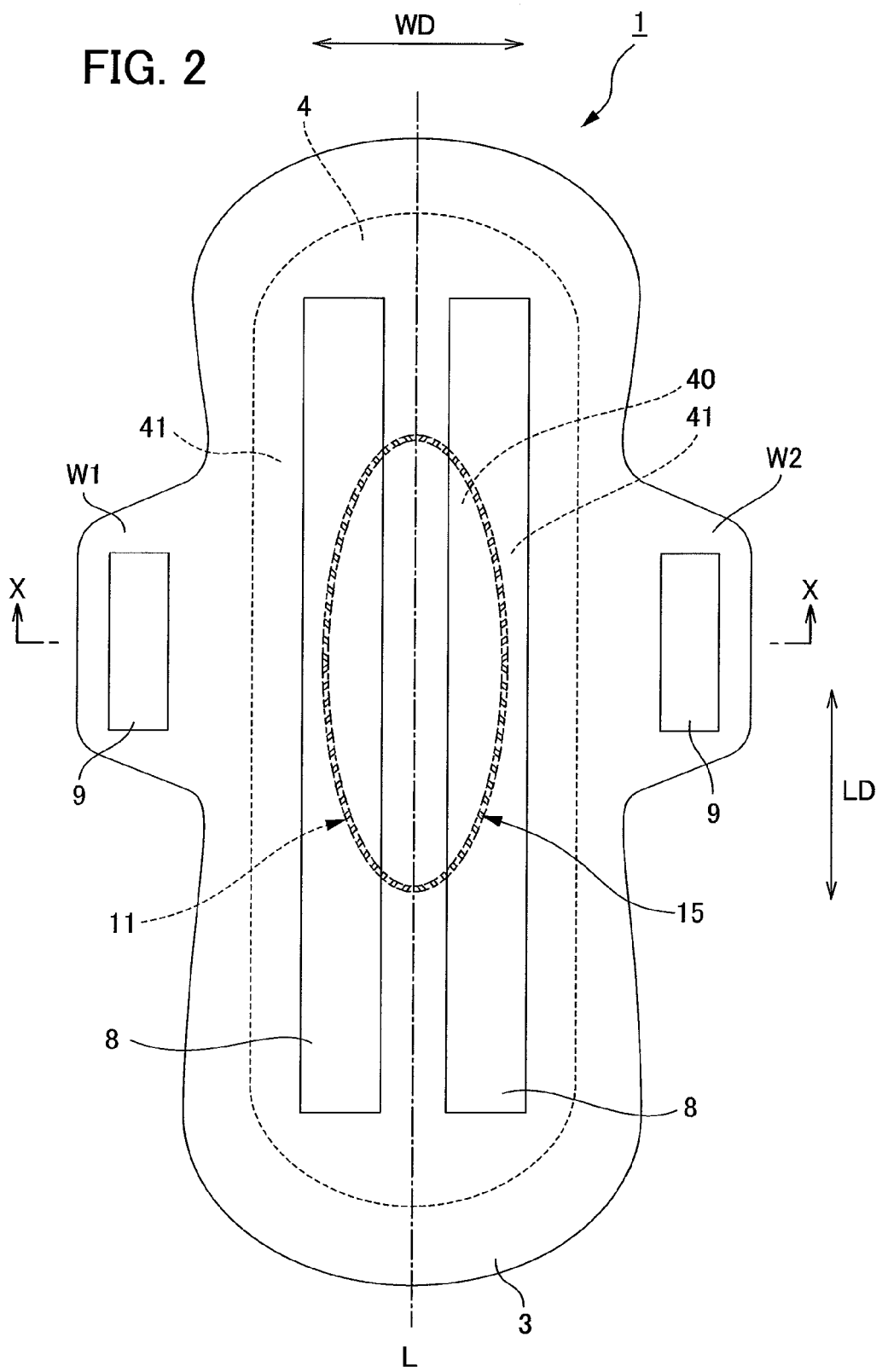
FIG. 2 is a back view of FIG. 1.
Figure 3:
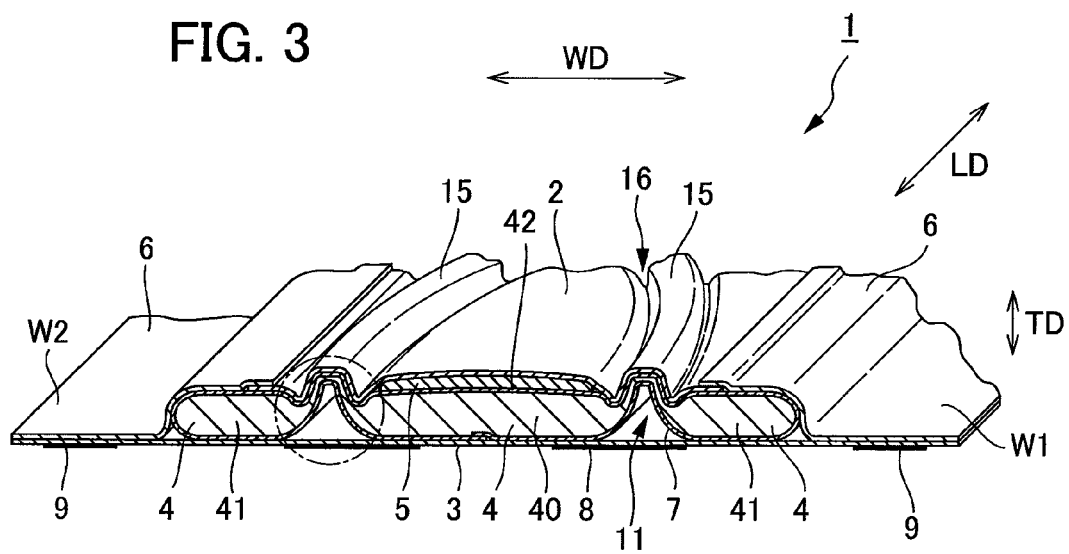
FIG. 3 is a diagram illustrating FIG. 1, showing a cross section taken along the line X-X.
Figure 4:
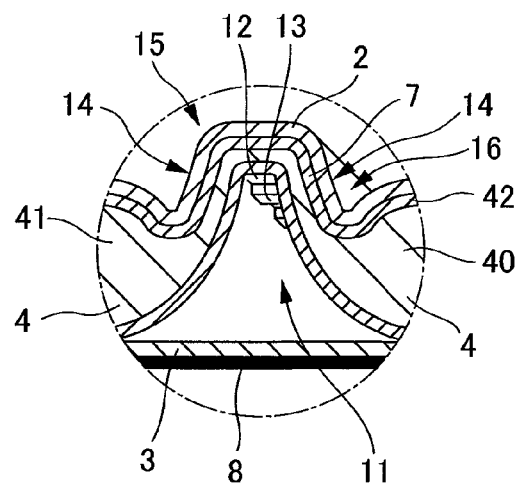
FIG. 4 is a partially enlarged view of FIG. 3.
Figure 5:
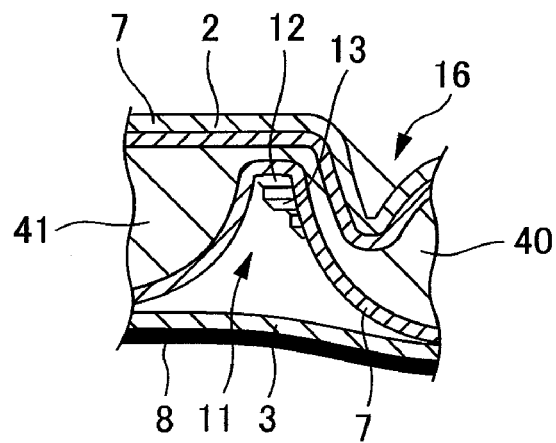
FIG. 5 is a diagram showing another aspect of a compressed groove.
Figure 6:
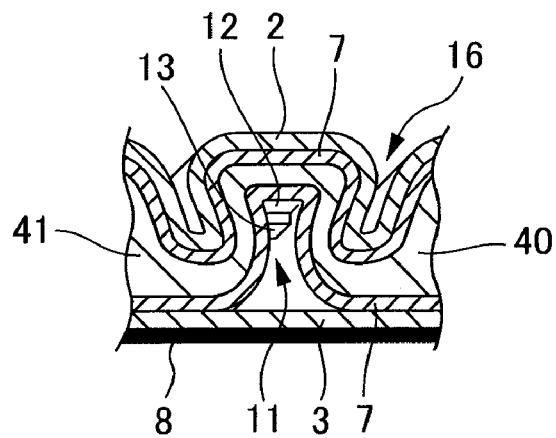
FIG. 6 is a diagram showing a compressed groove of a sanitary napkin according to the first embodiment.
Figure 7A:
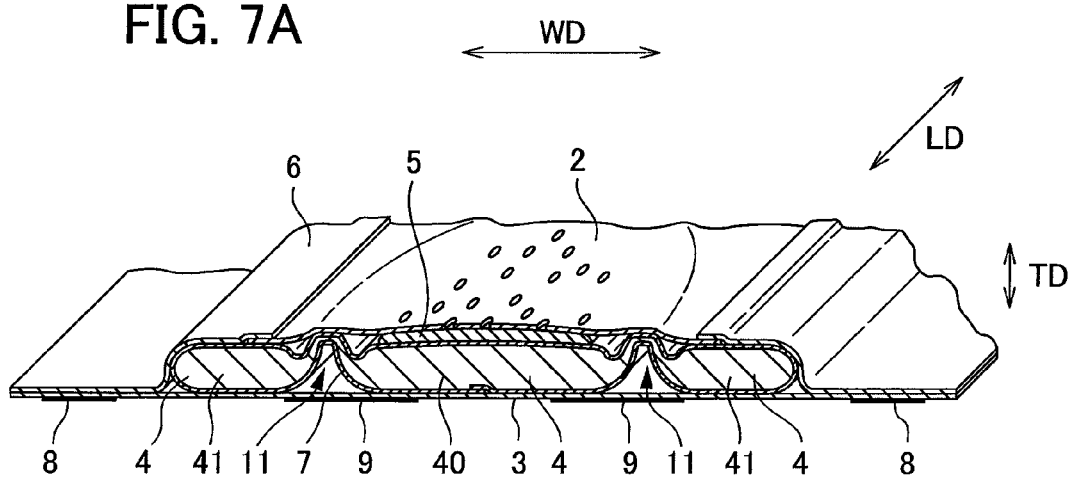
FIG. 7A is a diagram showing another aspect of the sanitary napkin according to the first embodiment.
Figure 7B:
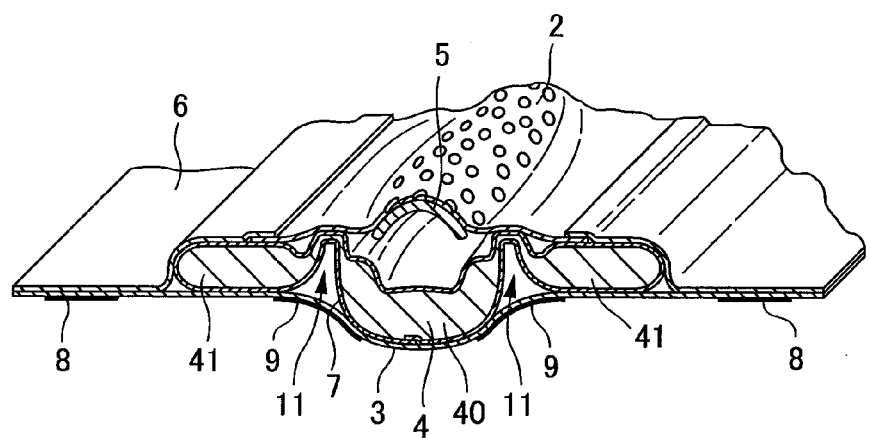
FIG. 7B is a diagram showing a deformed state of FIG. 7A.
Figure 8:
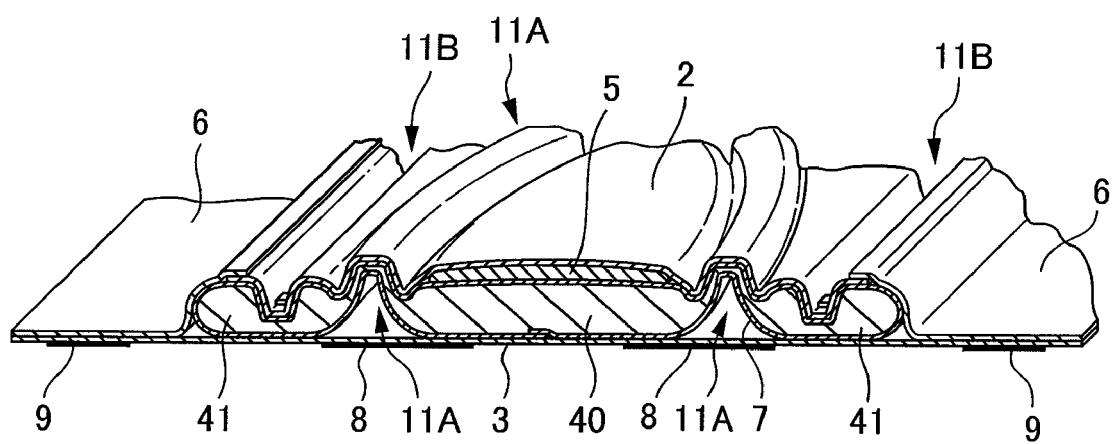
FIG. 8 is a diagram showing another aspect of an arrangement of the compressed groove.
Figure 9A:
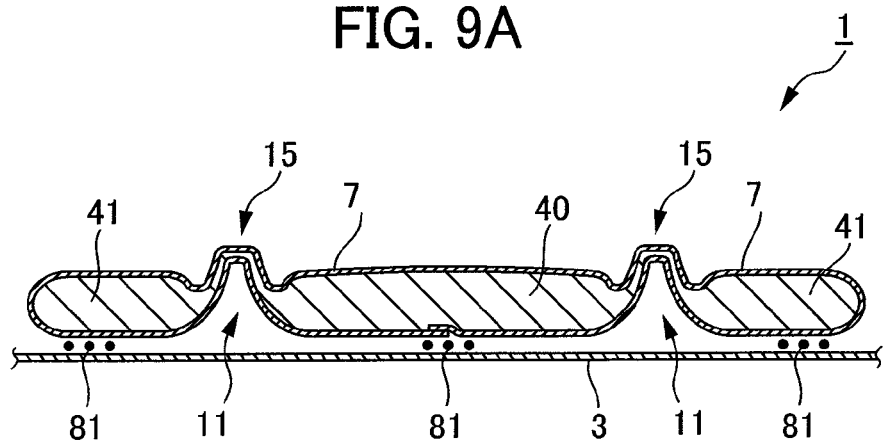
FIG. 9A is a diagram showing a relationship regarding joining of an absorbent core and a back sheet.
Figure 9B:
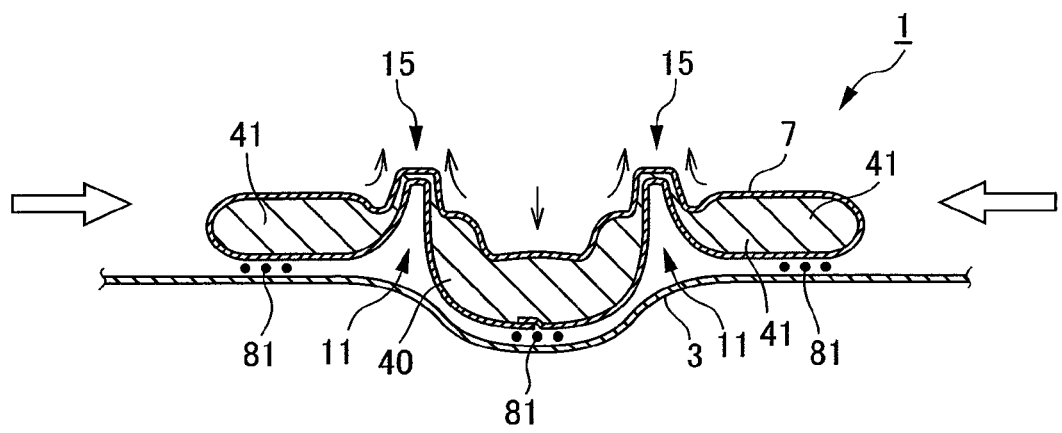
FIG. 9B is a diagram showing a deformed state of FIG. 9A.
Figure 10A:
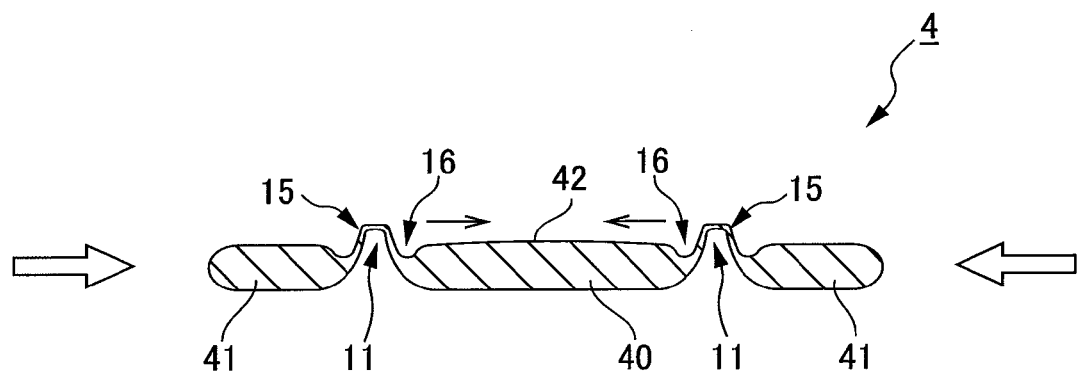
FIG. 10A is a diagram showing a deformed state of the sanitary napkin according to the first embodiment.
Figure 10B:
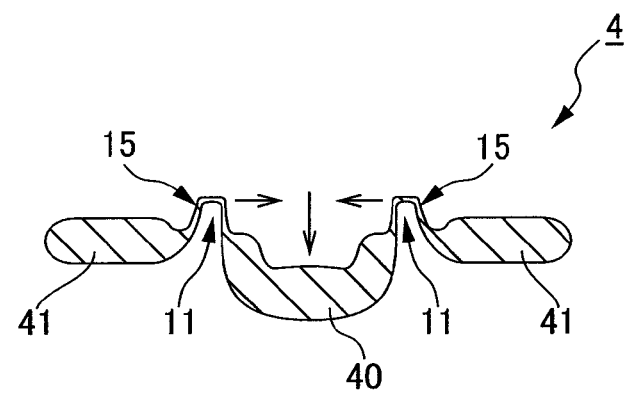
FIG. 10B is a diagram showing a deformed state of the sanitary napkin according to the first embodiment.
Figure 11A:
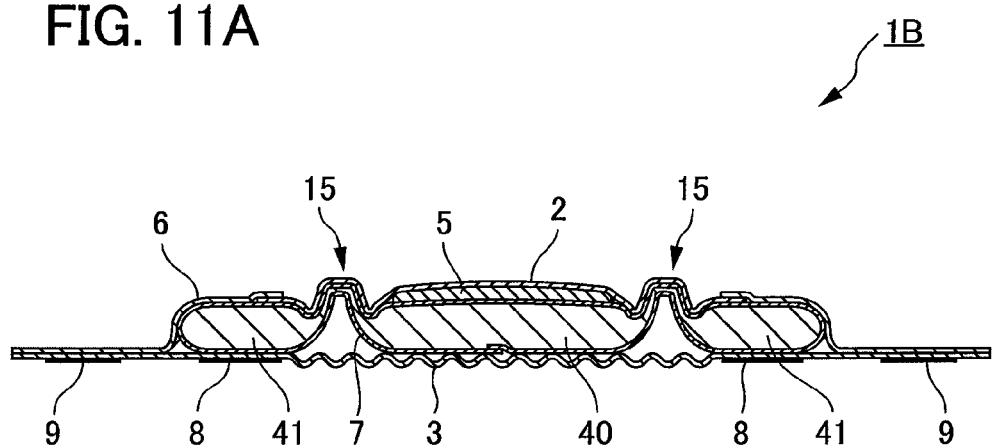
FIG. 11A is a cross-sectional view showing the sanitary napkin according to a second embodiment of the present invention.
Figure 11B:
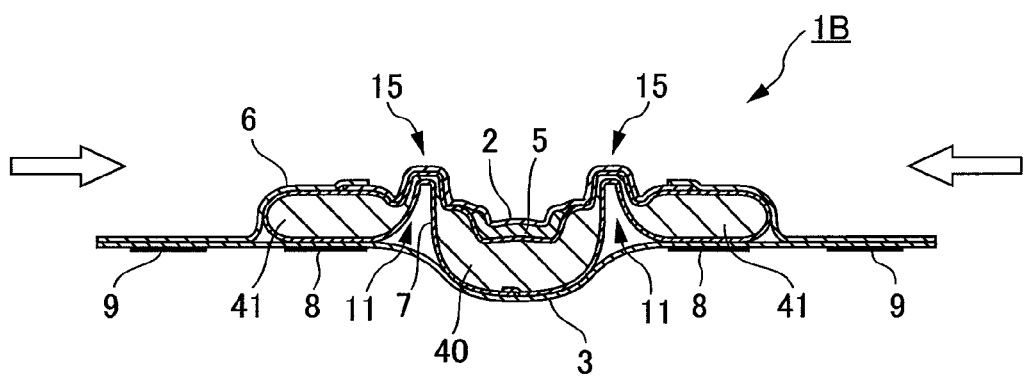
FIG. 11B is a diagram showing a deformed state of FIG. 11A.
Figure 12A:
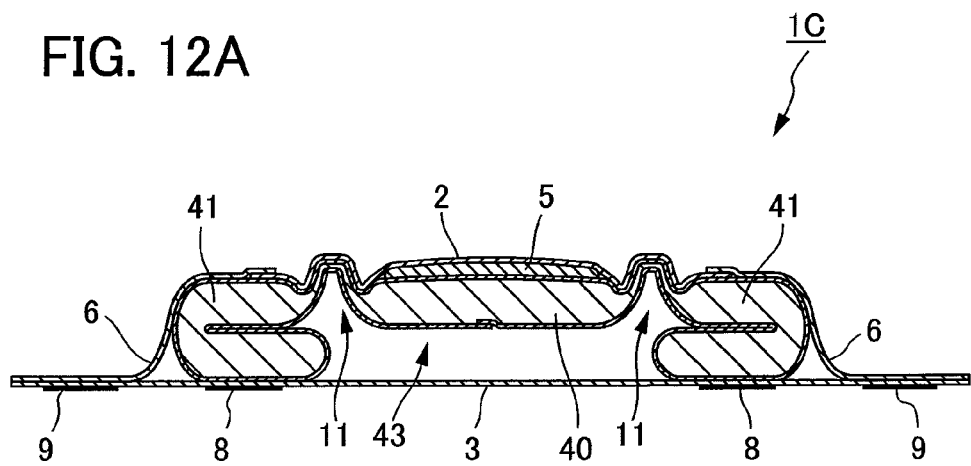
FIG. 12A is a cross-sectional view showing the sanitary napkin according to a third embodiment of the present invention.
Figure 12B:
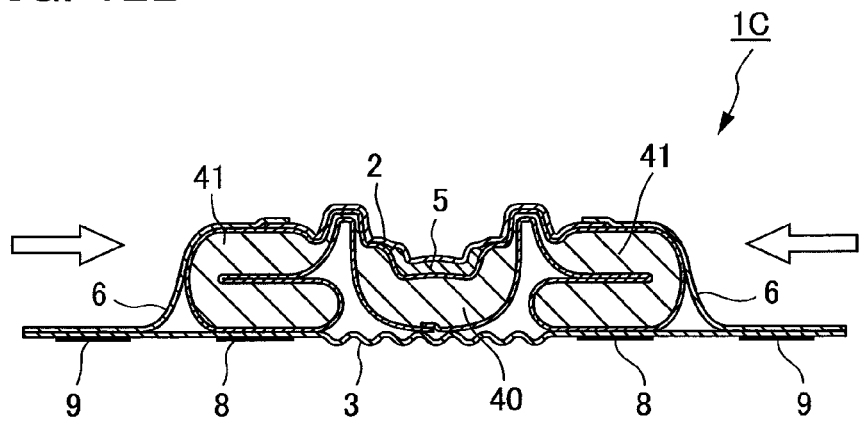
FIG. 12B is a diagram showing a deformed state of FIG. 12A.
Figure 13:
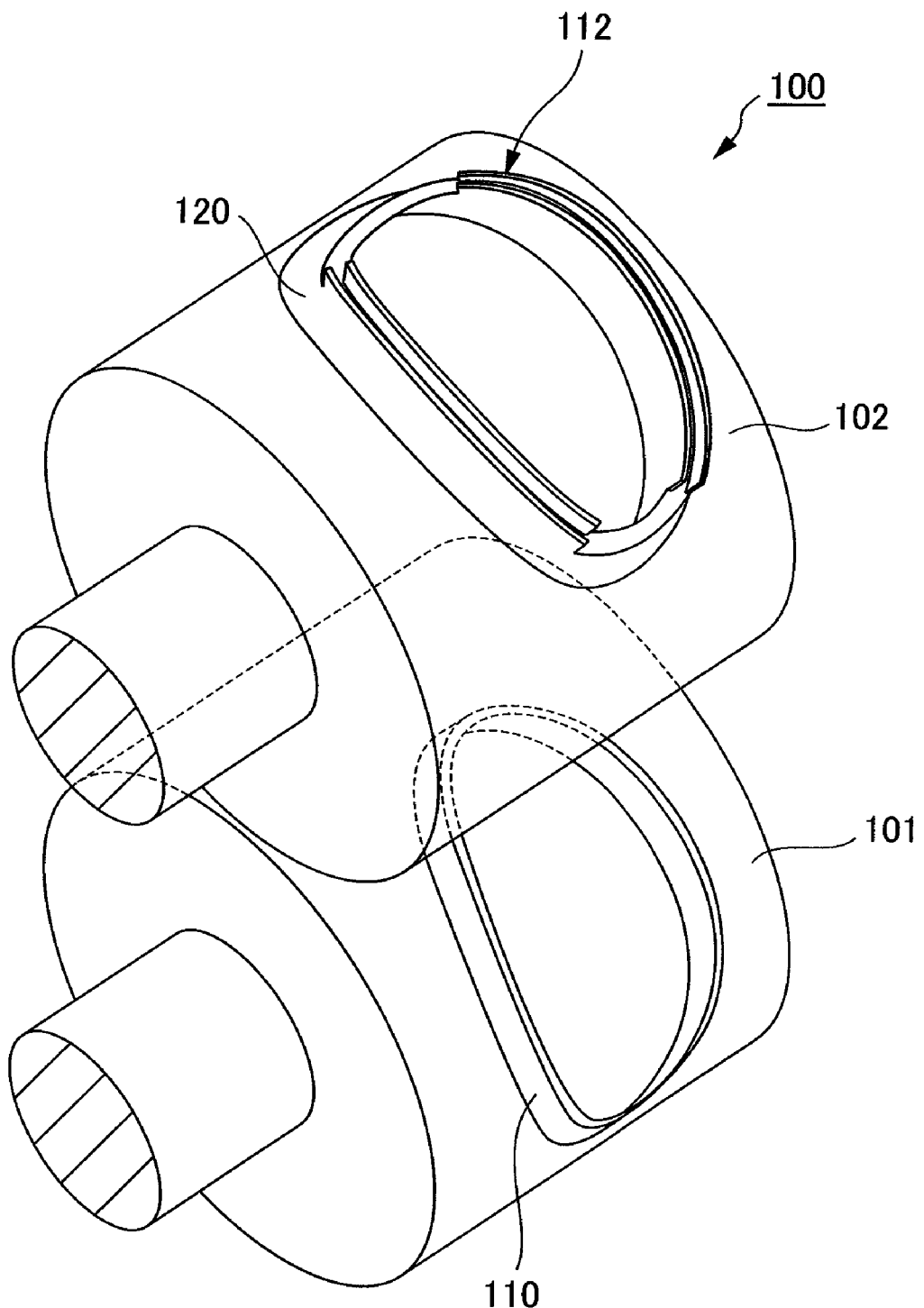
FIG. 13 is a diagram showing an embossing device according to the first embodiment.
Figure 14:
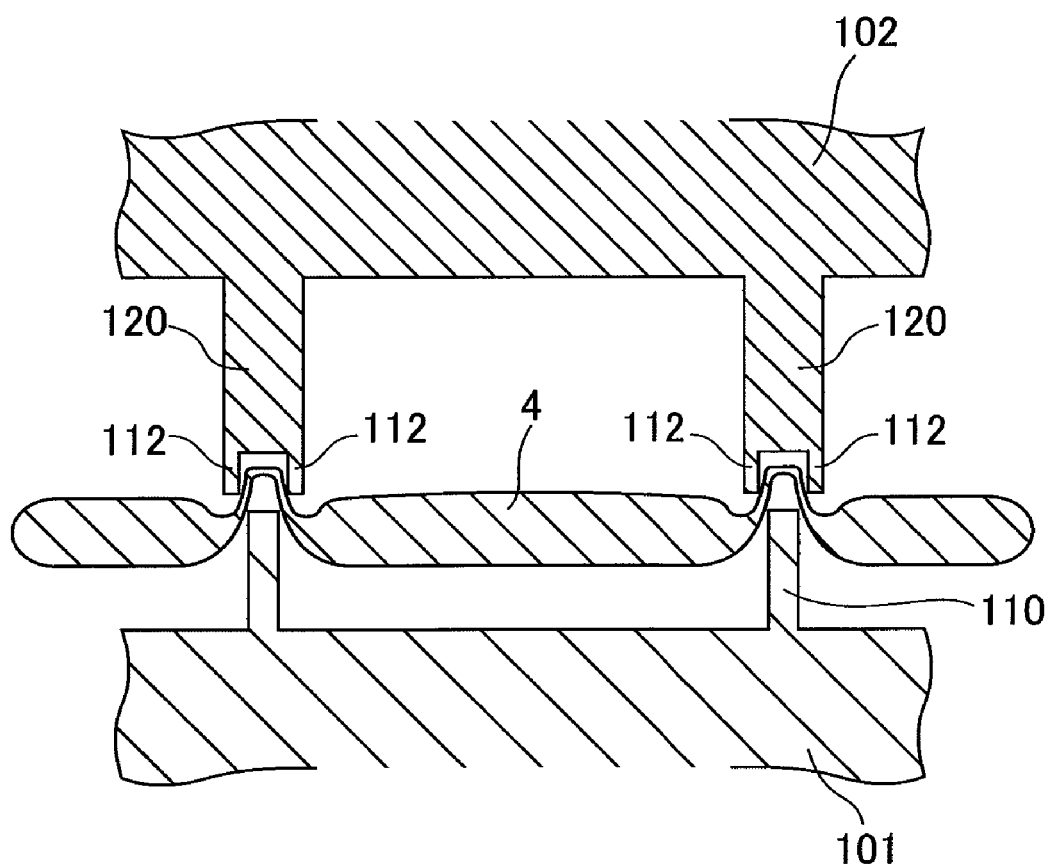
FIG. 14 is a diagram showing a state where the sanitary napkin is tucked by the embossing device.
Figure 15A:
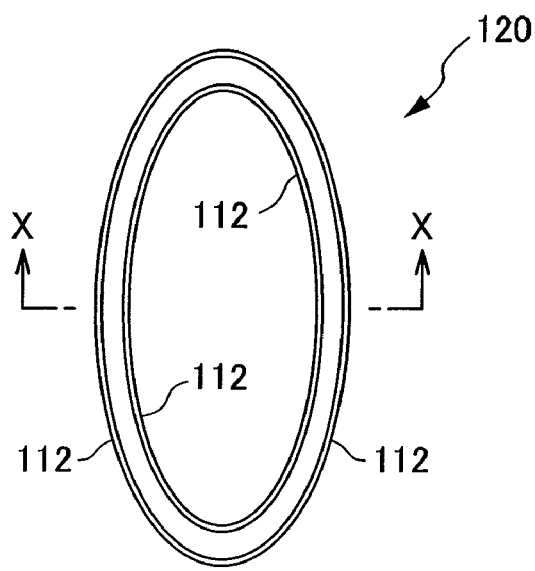
FIG. 15A is a diagram showing an upper embossing pattern on an upper embossing roller regarding the sanitary napkin according to the first preferred embodiment.
Figure 15B:
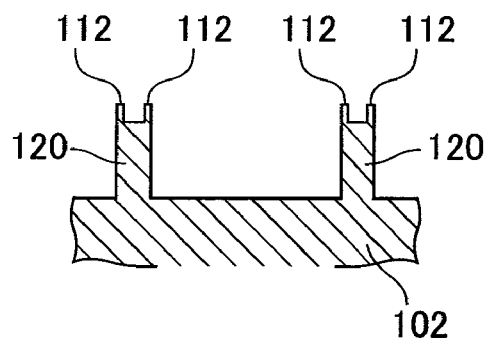
FIG. 15B is a sectional view taken along the line X-X of FIG. 15A.
Figure 16A:
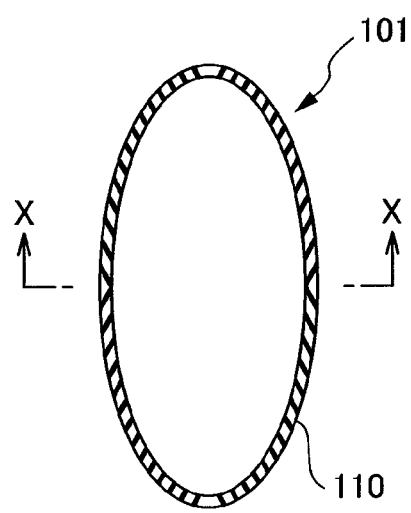
FIG. 16A is a diagram showing a lower embossing pattern on a lower embossing roller regarding the sanitary napkin according to the first preferred embodiment.
Figure 16B:
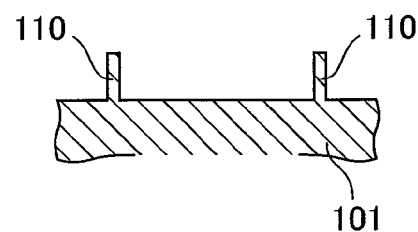
FIG. 16B is a sectional view taken along the line X-X of FIG. 16A.
Figure 16C:
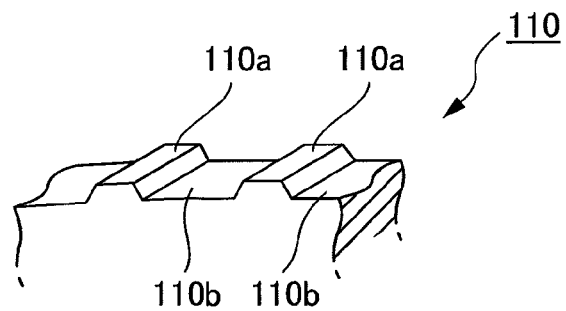
FIG. 16C is a partially enlarged view of FIG. 16B.
Figure 17:
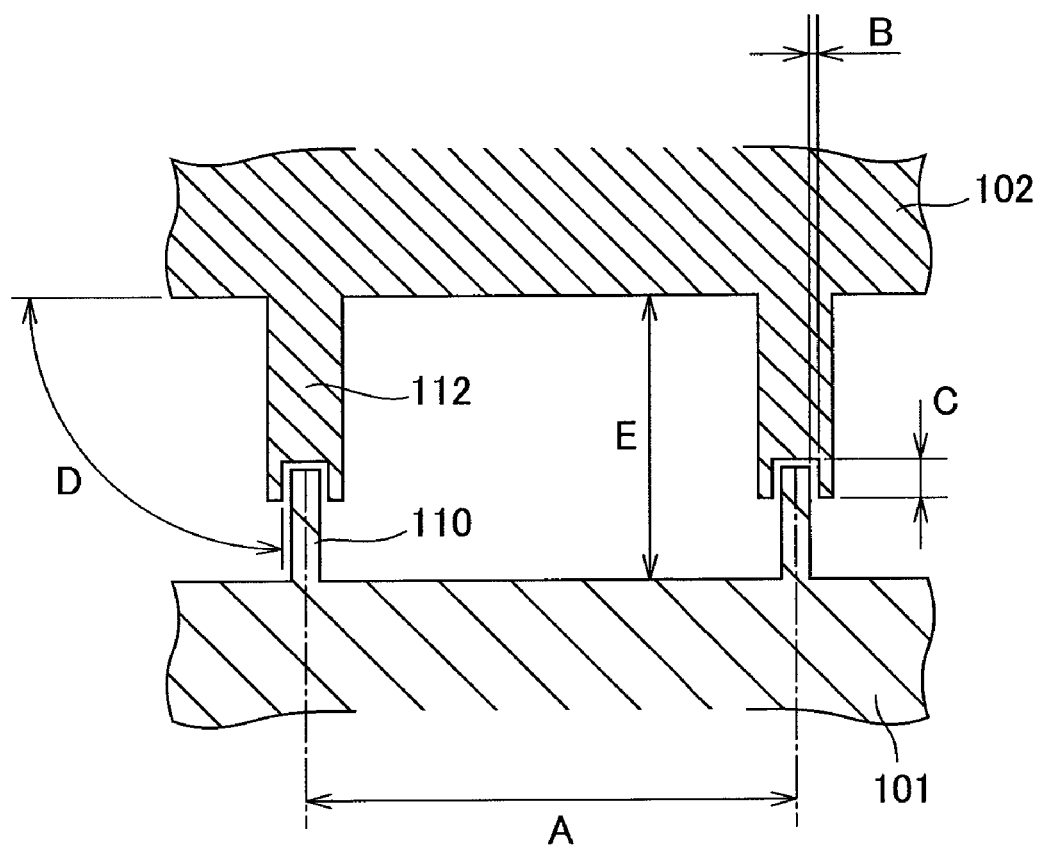
FIG. 17 is a diagram showing an interlocking portion of the embossing device for the sanitary napkin according to the first embodiment.

FIG. 1 is a plan view of a sanitary napkin according to a first embodiment of the present invention. FIG. 2 is a back view of FIG. 1. FIG. 3 is a diagram illustrating FIG. 1, showing a cross section taken along the line X-X. FIG. 4 is a partially enlarged view of FIG. 3. FIG. 5 is a diagram showing another aspect of a compressed groove. FIG. 6 is a diagram showing a compressed groove of a sanitary napkin according to the first embodiment. FIG. 7A is a diagram showing another aspect of the sanitary napkin according to the first embodiment. FIG. 7B is a diagram showing a deformed state of FIG. 7A. FIG. 8 is a diagram showing another aspect of arrangement of the compressed groove. FIG. 9A is a diagram showing a relationship regarding joining of an absorbent core and a back sheet. FIG. 9B is a diagram showing a deformed state of FIG. 9A. FIG. 10A is a diagram showing a deformed state of the sanitary napkin according to the first embodiment. FIG. 10B is a diagram showing a deformed state of the sanitary napkin according to the first embodiment. FIG. 11A is a cross-sectional view showing the sanitary napkin according to the second embodiment of the present invention. FIG. 11B is a diagram showing a deformed state of FIG. 11A. FIG. 12A is a cross-sectional view showing the sanitary napkin according to the third embodiment of the present invention. FIG. 12B is a diagram showing a deformed state of FIG. 12A. FIG. 13 is a diagram showing an embossing device according to the first embodiment. FIG. 14 is a diagram showing a state where the sanitary napkin is tucked by the embossing device. FIG. 15A is a diagram showing an upper embossing pattern on an upper embossing roller regarding the sanitary napkin according to the first preferred embodiment. FIG. 15B is a sectional view taken along the line X-X of FIG. 15A. FIG. 16A is a diagram showing a lower embossing pattern on a lower embossing roller regarding the sanitary napkin according to the first preferred embodiment. FIG. 16B is a sectional view taken along the line X-X of FIG. 16A. FIG. 16C is a partially enlarged view of FIG. 16B. FIG. 17 is a diagram showing an engaging portion of the embossing device for the sanitary napkin according to the first embodiment.

1. First Embodiment

The overall configuration of the absorbent article of the present invention is described hereinafter based on a sanitary napkin 1 according to a first embodiment of the present invention.

1.1. General View

As shown in FIGS. 1 to 4, the sanitary napkin 1 has a liquid permeable top sheet 2 which constitutes a surface layer and is disposed on the skin contacting side of a wearer, a liquid impermeable back sheet 3 which constitutes a back layer and is disposed on the clothing contacting side of the wearer, and a liquid retentive absorbent core 4 which is wrapped with a tissue 7 and constitutes an absorption layer. An adhesion portion 8 is provided on the clothing contacting side of the back sheet 3, which joins the sanitary napkin 1 with a wearer's underwear and the like. It should be noted that, in the first embodiment, the sanitary napkin 1 further includes an intermediate sheet 5 that is disposed between the top sheet 2 and the absorbent core 4, a side sheet 6 that constitutes a part of the surface layer, and side flaps W1 and W2 that extend in a width direction (WD) of the sanitary napkin 1. An adhesion portion 9 is provided on each of the side flaps W1 and W2, which allows the side flaps to be joined with underwear in a state of being folded back.

The sanitary napkin 1 further includes a compressed portion 11 that is formed on the clothing contacting side of the back sheet 3 in a convex shape toward the top sheet 2, and a break portion 16 that is formed on the skin contacting side of the top sheet 2 in a concave shape toward the back sheet 3. The compressed portion 11 is formed such that a high compression portion 12, which is formed with high compression, and a low compression portion 13, which is formed with low compression, are connected and surround a central core portion 40 that is formed substantially in a center of the absorbent core 4. In addition, the compressed portion 11 is provided with a projecting portion 15 that projects toward the skin contacting side, on the skin contacting side of the absorbent core 4. The break portion 16 is formed on both sides of the projecting portion 15 on the skin contacting side.

1.2. Top Sheet and Other Sheets

The top sheet 2 is disposed on the wearer's body side, and is also brought into contact with the excretory part during use. The top sheet 2 may be entirely or partially liquid permeable. In addition, the top sheet 2 may be composed of either a single sheet member or a plurality of sheet members joined together. In the present embodiment, the top sheet 2 has a liquid permeable region substantially in a center in the width direction (WD) of the sanitary napkin 1, and end portions thereof in the width direction (WD) are covered with the side sheet 6 that is liquid impermeable.

The intermediate sheet 5 lets through the discharged matter having passed through the top sheet 2 toward the absorbent core 4, while acting as a cushion during use. The sheet member for the top sheet 2 can also be used for the intermediate sheet 5.

The absorbent core 4 is wrapped with the tissue 7 and includes the central core portion 40, which is substantially elliptical, substantially in a center in the width direction (WD) of the sanitary napkin 1. The central core portion 40 is a region that is surrounded by the compressed portion 11. A side portion 41 is formed on both sides of the central core portion 40 in the width direction (WD). The central core portion 40 and the side portion 41 are separated by the compressed portion 11. The back sheet 3 prevents leakage of discharged matter and the like retained by the absorbent core 4 toward the clothing contacting side, by using a liquid impermeable sheet member.

Both side portions of the sanitary napkin 1, for example, the liquid impermeable sheet member disposed from the skin contacting side of the side portion 31 to the surface layer, and a part of the back sheet 3 extend outward in the width direction (WD), and an extended portion of the liquid impermeable sheet member and an extended portion of the back sheet 3 are joined by way of a hot melt adhesive and the like, thereby forming the side sheet 6.

1.3. Compressed Portion, Projecting Portion and Break Portion

The sanitary napkin 1 includes the compressed portion 11 that facilitates concave deformation of the central core portion 40. The compressed portion 11 is formed by compressing the top sheet 2 and the absorbent core 4 from the skin contacting side and a skin noncontacting side, and is disposed to extend in a longitudinal direction (LD) of the sanitary napkin 1, on both sides of the absorbent core 4 in the width direction (WD) across the central core portion 40.

The compressed portion 11 is formed by, for example, as shown in FIG. 4, respectively compressing at high compression and low compression alternately to be continuous. In addition, on the skin contacting side, the compressed portion 11 projects more towards the skin contacting side than a core surface portion 40, which is a skin contacting side of the central core portion 40, thereby forming the projecting portion 15 on the skin contacting side. On both sides across the projecting portion 15, i.e. between the central core portion 40 and the projecting portion 15 and between the side portion 41 and the projecting portion 15, the break portion 16 is formed along the projecting portion 15.

The break portion 16 is formed on both sides across the projecting portion 15 on the skin contacting side of the sanitary napkin, so as to be concave toward the clothing contacting side. The break portion 16 is formed such that, for example, an apex thereof is located 2 mm closer to the clothing contacting side than the core surface portion 42 of the central core portion 40. In other words, the break portion is formed such that a difference in height, in a thickness direction of the absorbent core 4, between the high compression portion 12 formed at the apex of the compressed portion 11 and a bottom portion of the break portion 16 is 2 mm. Preferably, a difference in height, in a thickness direction of the absorbent core 4, between the low compression portion 13 formed at the apex of the compressed portion 11 and a bottom portion of the break portion 16 is in a range of 0.5 to 10 mm, for example. If the difference in height, in a thickness direction of the absorbent core 4, from a bottom portion of the break portion 16 is in a range of 0.5 to 10 mm, the projecting portion 15 can more easily enter a concave groove 16 (break portion 16) formed on a skin contacting side of the central core portion 40.

It should be noted that, although the break portion 16 is provided on both sides across the projecting portion 15 in the present embodiment, the break portion can also be formed, for example, only on a side to the central core portion 40, as shown in FIG. 5. This configuration allows for the projecting portion 15 to bend toward the central core portion 40, which is a side to the break portion 16. In other words, this configuration can tilt the projecting portion 15 toward a center in the width direction (WD) of the absorbent article, starting from the break portion 16. It should be noted that the break portion 16 is preferably formed at a position closer to the compressed portion 11 than a center line (L) in a longitudinal direction (LD). This configuration can maintain a deformed state and thereby improve adhesion to skin.

The projecting portion 15 is formed to project more toward the skin contacting side than the core surface portion 42 of the central core portion 40. For example, the high compression portion 12 formed at the apex of the compressed portion 11 may be located 1 mm closer to the skin contacting side than the core surface portion 42 of the central core portion 40. In other words, a difference in height, in the thickness direction, between the high compression portion 12 of the compressed portion 11 and the core surface portion 42 of the central core portion 40 can be 1 mm. Preferably, a difference in height in a thickness direction between the high compression portion 12 and the core surface portion 42 is in a range of 0.5 to 10 mm, for example. If the difference in height, in a thickness direction, from the core surface portion 42 of the central core portion 40 is in a range of 0.5 to 10 mm, the projecting portion 15 can more easily enter the break portion 16 formed on a skin contacting side of the central core portion 40. In addition, a difference in height, in the thickness direction, between the low compression portion 13 of the compressed portion 11 and the core surface portion 42 of the central core portion 40 can be 1 mm.

The compressed portion 11 is provided with a pair of wall portions 14, which is formed by interlocking by way of an embossing device (described later). The wall portion 14 is formed by, for example, great tensile stress generated substantially in a center in the thickness direction of the sanitary napkin 1 in a case where the top sheet 2 and the absorbent core 4 is compressed in the thickness direction of the sanitary napkin 1, which stretches the absorbent core 4. In addition, the wall portion 14, which is formed by stretching the absorbent core 4, is low-density substantially in a center thereof. This low-density portion can suppress dispersion of discharged matter that is transferred from a high-density portion, in a case where the central core portion 40 absorbs discharged matter.

The compressed portion 11 is formed by continuously compressing the top sheet 2 and the absorbent core 4 from the skin contacting side and from the clothing contacting side; however, the present invention is not limited thereto. For example, as shown in FIG. 7A, a first compressed groove 11 (compressed portion 11) and the break portion 16 can be formed by continuously compressing only the absorbent core 4, from the skin contacting side and from the clothing contacting side. By forming in this way the compressed portion 11 and the break portion 16 only on the absorbent core 4, the central core portion 40 can deform more easily since the top sheet 2 does not hold the absorbent core 4 due to compression (see FIG. 7B). In addition, the compressed portion 11 and the break portion 16 can also be formed by continuously compressing the intermediate sheet 5 and the absorbent core 4, from the skin contacting side and from the clothing contacting side. For example, by continuously compressing the intermediate sheet 5, which is composed of synthetic resin fibers and the like, and the absorbent core 4, from the skin contacting side and from the clothing contacting side, a shape where the projecting portion 15 of the compressed portion 11 projects toward the skin contacting side can be easily maintained.

The compressed portion 11 and the break portion 16 are formed, for example, in a substantially elliptical shape around the central core portion 40 on the clothing contacting side of the sanitary napkin 1; however, the present invention is not limited thereto. The compressed portion 11 and the break portion 16 can also be formed across the core portion 40 to extend in the longitudinal direction of the sanitary napkin 1 and to become wider substantially in a center. In addition, the compressed portion 11 and the break portion 16 can also be formed across the central core portion 40 to extend in the longitudinal direction of the sanitary napkin 1 and to become narrower substantially in a center. Furthermore, as shown in FIG. 9, the compressed portion 11 can be formed on each of the skin contacting side and the clothing contacting side.

In the compressed portion 11, for example, the high compression portion 12 by a high compression and the low compression portion 13 by a low compression are each alternately formed to be continuous; however, the present invention is not limited thereto. For example, the compressed portion 11 can be composed only of the high compression portion 12 or the low compression portion 13, and configured to have a constant height without unevenness. In addition, in the compressed portion 11, the high compression portion 12 and the low compression portion 13 may not be formed continuously, but rather be formed at predetermined intervals. Furthermore, different combinations of embossing patterns can also be used. Moreover, the high compression portion 12 or the low compression portion 13 can be provided not entirely, but partially in the width of the compressed portion 11 in the width direction. Moreover, the high compression portion 12 or the low compression portion 13 can be provided not entirely, but partially in the width of the compressed portion 11 in the width direction.

1.4. Relationship with Back Sheet

As shown in FIG. 9A, in the first embodiment, the absorbent core 4 and the back sheet 3 are joined by a hot melt adhesive 81 in the central core portion 40 and the side portion 41. In other words, the absorbent core 4 and the back sheet 3 are not joined in the compressed portion 11. By thus joining the absorbent core 4 and the back sheet 3 in areas other than the compressed portion 11, for example, in a case where the central core portion 40 deforms into a concave shape under a compressive force in the width direction (WD) applied from a wearer's thighs, the compressed portion 11 can easily move in a direction away from the back sheet 3 (toward the skin contacting side) thereby forming a large space in the central core portion 40 (see FIG. 9B).

1.5. Operation

The sanitary napkin 1 can deform into a concave shape, for example, where a substantially central portion of the central core portion 40 projects toward the clothing contacting side, by providing the compressed portion 11 and the break portion 16 on the absorbent core 4. For example, under a compressive force applied from the wearer's thighs, a compressive force is applied in a direction of an arrow shown in FIG. 10A. Here, the compressive force is transferred to the central core portion 40 via the compressed portion 11. In other words, the compressive force is transferred to the central core portion 40 via the projecting portion 15. Here, the projecting portion 15, which is the skin contacting side of the compressed portion 11, tilts toward the skin contacting side and deforms to slide into a side to the core surface portion 42 of the central core portion 40, since the break portion 16 is formed on a side to the central core portion 40. In other words, after contacting the wearer's skin, the projecting portion 15 moves to slide into the break portion 16 formed between the compressed portion 11 and the core surface portion 42 of the central core portion 40 that is adjacent thereto. The projecting portion 15, after moving to slide into the break portion 16, further moves to the central core portion 40 so as to push the central core portion 40 from the core surface portion 42 of the central core portion 40 into the clothing contacting side, thus transferring stress to the central core portion 40. This deforms the central core portion 40 into a concave shape, such that a substantially central portion thereof projects toward the clothing contacting side (see FIG. 10B). Here, the projecting portion 15 also moves toward the skin contacting side and makes contact with the vicinity of the wearer's excretory part, thereby avoiding dispersion of bodily fluid and the like discharged therefrom.

2. Other Embodiments

Second and third embodiments of the present invention are described hereinafter with reference to FIGS. 11A to 12B. In the second embodiment, the back sheet 3 has been processed for shape forming. In the third embodiment, a predetermined break portion is provided between the back sheet 3 and the absorbent core 4.

In the following description, the same reference numerals have been retained for similar parts that are identical to that described in the first embodiment, with the description thereof omitted.

2.1. Second Embodiment

A sanitary napkin 1B of the second embodiment of the present invention is described with reference to FIGS. 11A and 11B. As illustrated in FIG. 11A, the sanitary napkin 1B is different from the first embodiment in that the back sheet 3 has been processed for shape forming. More specifically, the back sheet 3 used in the sanitary napkin 1B has been processed for shape forming and is corrugated, whereby convex portions and concave portions are arranged continuously in a longitudinal direction of the sanitary napkin 1B.

Here, in the sanitary napkin 1B according to the present invention, the clothing contacting side of the central core portion 40 is required to be easily projected toward the clothing contacting side, in order to deform the central core portion 40 into a concave shape. To facilitate such a deformation of the central core portion 40, the back sheet 3, which is disposed on a skin noncontacting side of the central core portion 40, is preferably formed to be easily stretched in a width direction (WD). This is to prevent the back sheet 3 from holding the central core portion 40.

Given this, in the sanitary napkin 1B according to the second embodiment, the back sheet 3 is processed to be corrugated and stretchable in the width direction (WD). This can prevent the back sheet 3 from holding the central core portion 40 and facilitate deformation to project the central core portion 40 as shown in FIG. 11B.

It should be noted that, although the back sheet 3 is processed to be corrugated and configured to be stretchable in the width direction (WD) in the sanitary napkin 1B according to the second embodiment, the present invention is not limited thereto. For example, the back sheet 3 can be made stretchable by providing gathers (not shown) that are non-joined or weakly joined. In this way, by providing the non-joined or weakly joined gathers on the back sheet 3, in a case where the central core portion 40 is deformed into a concave shape, the back sheet can extend to the width direction (WD) within a width of gathers provided thereon and the central core portion 40 can be easily deformed into a concave shape without being held by the back sheet 3. The gathers are provided in at least a portion of the clothing contacting side, in any position thereon.

In addition, aside from processing the back sheet 3, the back sheet 3 can be made inherently stretchable in the width direction (WD) with coiled crimped fiber or stretchable fiber such as urethane, or with a smaller number of fusion points. Furthermore, the back sheet 3 can be made with s fiber orientation in which more fibers are oriented in the longitudinal direction (LD), thus lowering tensile strength in the width direction (WD) and providing stretchability.

2.2. Third Embodiment

A sanitary napkin 1C of the third embodiment of the present invention is described with reference to FIGS. 12A and 12B. As illustrated in FIG. 12A, the sanitary napkin 1C is different from the first embodiment in that a predetermined break portion 43 is formed between the back sheet 3 and the central core portion 40. More specifically, the sanitary napkin 1C includes a break portion 43 that is formed by turning up each of the side portions 41 of the absorbent core 4, from the clothing contacting side, toward a center in the width direction (WD) of the absorbent core 4, thereby making a thickness in the side portion 41 greater than a thickness in the central core portion 40.

In this way, by providing the break portion 43 between the back sheet 3 and the central core portion 40, in a case where the central core portion 40 is deformed into a concave shape, the clothing contacting side of the central core portion 40 can enter the break portion 43 and facilitate the concave deformation of the central core portion 40 (see FIG. 12B).

It should be noted that, in the third embodiment, although the break portion 43 is formed by turning up each of the side portions 41 of the absorbent core 4 from the clothing contacting side toward a center in the width direction (WD) of the absorbent core 4, thereby making a thickness in the side portion 41 greater than a thickness in the central core portion 40, the present invention is not limited thereto. For example, the break portion 43 between the central core portion 40 and the back sheet 3 can also be formed by adjusting a height of the side portion 41 in the thickness direction by increasing a basis weight in the side portion 41. In addition, the break portion 43 between the central core portion 40 and the back sheet 3 can also be formed by disposing another member that is independent from the side portion 41, on the clothing contacting side of the side portion 41. The other member 44 can be made of either the same or different material as that of the absorbent core.

3. Components

Hereinafter, each structural component is described.

3.1. Top Sheet

The top sheet 2 can be made of, for example, a resin film on which a plurality of liquid passage holes is formed as in a liquid permeable region constituting at least a portion of the top sheet 2, a net sheet having a plurality of mesh pores, a liquid-permeable nonwoven fabric, or a liquid-permeable fabric. A resin film or the net sheet formed of polypropylene (PP), polyethylene (PE), polyethylene terephthalate (PET), and so on can be used. As the nonwoven fabric, a spun-laced nonwoven fabric made of cellulose fibers such as rayon and synthetic resin fibers, and an air-through nonwoven fabric made of the synthetic resin fibers can be used, for example. For an air-through nonwoven fabric having a gap between fibers, for example, a synthetic fiber of a hydrophilic fiber and a hydrophobic fiber can be used.

It should be noted that, in consideration of liquid drawing ability, it is preferable that: a coarse-dense gradient, in which a density of a portion of the top sheet 2 is higher than a periphery thereof, is provided to the top sheet 2; the top sheet 2 itself is formed to have a coarse-dense gradient; or the top sheet 2 is formed to have areas of different hydrophilic properties.

3.2. Intermediate Sheet

The intermediate sheet 5 is a liquid permeable sheet disposed between the top sheet 2 and the absorbent core 4, which acts as a supporting body of the absorbent core 4 and provides the absorbent core 4 with flexibility and stability in shape. The intermediate sheet 5 can be made of the same material as used in the top sheet 2. It should be noted that, in consideration of liquid drawing ability, it is preferable that: a coarse-dense gradient, in which a density of a portion of the intermediate sheet 5 is higher than a periphery thereof, is provided to the intermediate sheet 5; the intermediate sheet 5 itself is formed to have a coarse-dense gradient; or portions of the intermediate sheet 5 are formed to have different hydrophilic properties.

3.3. Absorbent Core

Although the absorbent core 4 used in the present embodiment is prepared by wrapping pulverized kraft pulp with 3% of high absorbance polymer blended therein with the tissue 7, the present invention is not limited thereto. For example, the absorbent core 4 can be made of pulverized pulp with a heat adhesive synthetic fiber blended therein, an air-laid or pulp sheet-like member, a spun lace made of cotton, rayon, pulp and the like, or a mixture thereof. In addition, a urethane or cellulose sponge, which has elasticity, can also be used. It should be noted that the present invention is not limited to the abovementioned materials and a combination thereof, and that any material, which is conventionally used as an absorbent core, can be used.

3.4. Back Sheet

The back sheet 3 is made of a material capable of preventing leakage of a discharged matter once absorbed by the absorbent core 4. In addition, the back sheet 3 may be made of a moisture-permeable material, in order to suppress a humid condition and feeling of discomfort during use. As such a material, a liquid impermeable polyethylene (PE) sheet is used for the back sheet 3 according to the present embodiment; however, the present invention is not limited thereto. For example the back sheet 3 can be made of: a resin film made of any one of, or a combination of two of, polyethylene (PE), polypropylene (PP), polyethylene terephthalate (PET), and EVA resin; a film obtained by adding a filler and the like to the abovementioned resin film, and stretching to form microperforations thereon in order to provide moisture permeability; a laminated member made of resin and paper; a sheet obtained by laminating a nonwoven fabric and a resin film. Preferably, a hydrophobic nonwoven fabric, a liquid impermeable plastic film, a laminated sheet made of the nonwoven fabric and the liquid impermeable plastic film, and the like can be used. Alternatively, an SMS nonwoven fabric sandwiched by a melt-blown nonwoven fabric of high water-resistance and a high-strength spun-bonded nonwoven fabric may also be used. More preferably, a material of high tensile property may be used, for example, a water repellent nonwoven fabric made of elastic urethane, or a thermally crimpable fiber that is heated to be coiled and stretchable, and then processed to be waterproof.

3.5. Adhesive Body

An adhesive body used in the adhesive portions 8 and 9 for preventing dislocation is a rubber-based hot melt adhesive; however, the present invention is not limited thereto and an olefin-based hot melt adhesive, a mechanical fastener, a styrene rubber-based anti-slip agent and the like can also be used.

4. Manufacturing Equipment

The sanitary napkin 1 according to the present invention is formed, for example, by way of an embossing device 100 including a pair of embossing rollers 101 and 102 shown in FIGS. 13 to 17. As shown in FIGS. 13 and 14, the pair of embossing rollers 101 and 102 includes an upper embossing roller 102 and a lower embossing roller 101. Each of the upper embossing roller 102 and the lower embossing roller 101 rotates at a predetermined rotation speed and forms the compressed groove 11 (compressed portion 11) according to the present embodiment when the sanitary napkin 1 passes between the upper embossing roller 102 and the lower embossing roller 101 under a predetermined pressure and predetermined heat.

As shown in FIGS. 15A and 15B, the upper embossing roller 102 includes an embossing tooth 120 having a pair of mesh embossing teeth 112, each of which is formed in a convex shape. In addition, as shown in FIGS. 16A and 16B, the lower embossing roller 101 includes a lower embossing pattern having embossing teeth 110 that are formed in a convex shape.

More specifically, as shown in FIG. 15A, in an upper embossing pattern, the paired embossing teeth 120, having the pair of mesh embossing teeth 112 on side edges thereof, is formed in an elliptical shape. In addition, as shown in FIG. 15B, between the pair of mesh embossing teeth 112, a concave portion is formed that can engage with the embossing teeth 110.

It should be noted that the embossing device 100 is configured not to crush the central core portion 40 by forming the embossing tooth 120 in a convex shape as shown in FIG. 14, thereby making a space substantially in a center thereof; however, the present invention is not limited thereto. For example, the embossing teeth 120 can be in a concave shape that can engage with the embossing teeth 110, as long as a shape can be obtained that does not crush the central core portion 40.

As the lower embossing pattern, a convex pattern as shown in FIGS. 16A and 16B can be exemplified. In the lower embossing pattern, the embossing teeth 110 are formed in a convex portion, which is inserted between and engages with the pair of mesh embossing teeth 112. In addition, as shown in FIG. 16C, the embossing teeth 110 are formed in a concave-convex shape in which a convex portion 110a and a concave portion 110b are formed to be consecutive. The convex portion 110a forms the high compression portion 12 and the concave portion 110b forms the low compression portion 13 in the compressed portion 11. It should be noted that, although the embossing teeth 110 are formed in a concave-convex shape in which the convex portion 110a and the concave portion 110b are formed consecutively, the present invention is not limited thereto. For example, the embossing teeth 110 can have a constant height without concave and convex portions.

In addition, the mesh embossing teeth 112 extend with a constant height, without concave and convex portions, in the present embodiment; however, the present invention is not limited thereto. For example, the mesh embossing teeth 112 can have different heights at least in a portion thereof, i.e. a convex portion and the concave portion that are formed consecutively. In other words, the mesh embossing teeth 112 can project intermittently, and not continuously. In this way, by providing a concave portion at least in a portion of the mesh embossing teeth 112, the projecting portion 15 in the compressed groove 11 (compressed portion 11) can maintain a shape thereof more reliably.

The compressed portion 11 and the break portion 16 according to the present embodiment are formed by engaging each of the upper embossing pattern and the lower embossing pattern with the sanitary napkin 1. More specifically, the compressed portion 11 and the break portion 16 are formed by engaging the mesh embossing teeth 112 of the upper embossing roller 102 and the mesh embossing teeth 110 of the lower embossing roller 101 in a thickness direction from the skin contacting side and from the clothing contacting side, respectively (see FIG. 14).

It should be noted that the embossing device 100 can use the embossing rollers 101 and 103 that are configured such that, for example, as shown in FIG. 17, a pitch A of the embossing teeth 112 on the upper embossing roller 102 is 37 mm; a distance B between the upper embossing roller 102 and the lower embossing roller 101 at an engaging portion is 0.70 mm; an engagement depth C for projecting the compressed groove 11 (compressed portion 11) upwards is 3.0 mm; an angle D of a lateral wall of the lower embossing roller 101 facing the compressed groove 11 (compressed portion 11) is 80°; and a distance E from a bottom face of the upper embossing roller 102 to a bottom face of the lower embossing roller 101 is 70 mm.

To allow the central core portion 40 to deform into a concave shape, the pitch A of the embossing teeth 112 on the upper embossing roller 102 is preferably in a range of 20 to 60 mm. More preferably, a range of 30 to 50 mm can be exemplified. The distance B between the upper embossing roller 102 and the lower embossing roller 101 at an engaging portion is preferably in a range of 0.3 to 10 mm. More preferably, a range of 0.5 to 5.0 mm can be exemplified. The engagement depth C for projecting the projecting region 15 of the compressed groove 11 (compressed portion 11) upwards is preferably in a range of 1 to 10 mm. More preferably, a range of 2 to 6 mm can be exemplified. The angle D of a lateral wall of the lower embossing roller 101 facing the compressed groove 11 (compressed portion 11) is preferably in a range of 30 to 120°. More preferably, a range of 45 to 100° can be exemplified. The distance E from a bottom face of the upper embossing roller 102 to a bottom face of the lower embossing roller 101 is preferably in a range of 5 to 30 mm. More preferably, a range of 8 to 15 mm can be exemplified.

In addition, a manufacturing equipment using an upper embossing roller 102 having a flat surface without a concave or convex portion, in a portion contacting the embossing teeth 110 of the lower embossing roller 101, which is made of a material that can become concave when being engaged with the lower embossing roller 101, can be used for realizing a similar embodiment. For example, a material that can change the height thereof under a compression force, such as paper and hard rubber, can be used.

5. Manufacturing Method

A method for manufacturing the sanitary napkin 1 according to the present invention is described hereinafter. The method for manufacturing the sanitary napkin 1 according to the present invention includes a compressed portion forming step in which the compressed portion 11 and the break portion 16 are formed by compressing the sanitary napkin 1 from the skin contacting side and the clothing contacting side. In compressed portion forming step, the embossing device 100 having: an upper die roller portion including the paired embossing tooth 120 having the pair of mesh embossing teeth 112 formed in a predetermined pattern on a surface thereof; and a bottom die roller portion including the mesh embossing teeth 110 formed thereon that can engage with the mesh embossing teeth 112 formed in the predetermined pattern on the upper die roller portion, forms the compressed portion 11 and the break portion 16 of the sanitary napkin 1 by compressing an absorbent article material, including at least the absorbent core 4, in a thickness direction.

On the sanitary napkin 1 according to the present invention, the compressed portion 11 that projects toward the skin contacting side is formed on the clothing contacting side, and the break portion 16 that is concave toward the clothing contacting side and the projecting portion 15 that projects toward the skin contacting side are formed on the skin contacting side by putting the sanitary napkin 1 through between the upper die roller portion having concave portions and the bottom die roller portion having convex portions, under a predetermined pressure and predetermined heat. The sanitary napkin material including at least the absorbent core 4 is compressed in a thickness direction (TD), by passing through between the upper die roller portion having concave portions and the bottom die roller portion having convex portions. The compression may be performed either in a continuous manner or at predetermined intervals.

The manufacturing method according to the present invention produces an absorbent article including: a top sheet that is at least partially liquid permeable and disposed on a skin contacting side; a back sheet that is liquid impermeable and disposed on a clothing contacting side; and an absorbent core, which is liquid retentive, disposed between the top sheet and the back sheet, in which the absorbent core includes a compressed portion that is formed on the clothing contacting side in a convex shape toward the skin contacting side by compression from the clothing contacting side to the skin contacting side and a break portion that is formed on the skin contacting side in a concave shape toward the clothing contacting side by compression from the skin contacting side to the clothing contacting side, and in which the break portion is formed at least on one side of a projecting portion on a skin contacting side, which is on a reverse side of the compressed portion.

It should be noted that, since the description for the embossing device 100 applies to the manufacturing method, a part corresponding thereto is omitted.

The invention claimed is:

1. An absorbent article, comprising:
    a top sheet that is at least partially liquid permeable and disposed on a skin contacting side;
    a back sheet that is liquid impermeable and disposed on a skin non-contacting side; and
    an absorbent core that is liquid retentive and disposed between the top sheet and the back sheet,
    wherein the absorbent core includes:
        a compressed portion that is formed on the skin non-contacting side in a convex shape projecting toward the skin contacting side by compression from the skin non-contacting side toward the skin contacting side;
        a break portion that is formed on the skin contacting side in a concave shape projecting toward the skin non-contacting side by compression from the skin contacting side toward the skin non-contacting side; and
        a projecting portion corresponding to the compressed portion and projecting from the skin non-contacting side toward the skin contacting side.

2. The absorbent article according to claim 1, wherein the absorbent core comprises a central core portion substantially in a center thereof, and
    wherein the break portion is arranged between the central core portion and the projecting portion in a transverse direction of the absorbent article.

3. The absorbent article according to claim 2, wherein the projecting portion is insertable into the break portion upon moving at least a part of the central core portion of the absorbent core from the skin contacting side toward the skin non-contacting side in use.

4. The absorbent article according to claim 2, further comprising another break portion wherein the projecting portion is arranged between the two break portions in the transverse direction.

5. The absorbent article according to claim 2, wherein the projecting portion is adapted to bend toward the central core portion upon moving at least a part of the central core portion of the absorbent core from the skin contacting side toward the skin non-contacting side in use.

6. The absorbent article according to claim 2, wherein, on the skin contacting side, the projecting portion projects beyond a core surface portion of the central core portion.

7. Equipment for manufacturing the absorbent article according to claim 1, comprising a compressed portion forming device for forming the compressed portion,
wherein the compressed portion forming device includes
an upper die roller portion having a concave portion formed on a surface thereof, and
a bottom die roller portion having a convex portion on a surface thereof that is configured to removably fit into the concave portion,
wherein the upper die roller portion and the bottom die roller portion are configured to form the compressed portion and the break portion by compressing at least the absorbent core that is tucked therebetween.

8. A method of manufacturing the absorbent article according to claim 1, comprising the steps of
compressing the absorbent core from the skin contacting side to the skin non-contacting side to form the break portion in the concave shape on the skin contacting side, and
compressing the absorbent core from skin non-contacting side toward the skin contacting side to form the compressed portion in the convex shape on the skin non-contacting side,
wherein the steps of compressing are performed simultaneously by an upper die roller portion having a concave portion formed on a surface thereof and a bottom die roller portion having a convex portion on a surface thereof that removably fits into the concave portion, and the compressed portion and the break portion are formed in the convex shape and the concave shape, respectively in a state where at least the absorbent core is tucked therebetween.

9. The absorbent article according to claim 1, wherein the break portion is arranged closer to the compressed portion than a longitudinal center line of the absorbent article bisecting the absorbent article in a transverse direction of the absorbent article.

10. The absorbent article according to claim 1, wherein the projecting portion has a closed shape at the skin contacting side of the absorbent article.

11. The absorbent article according to claim 1, wherein the compressed portion includes walls which project toward the skin contacting side and are defined by the top sheet and the absorbent core, both of which are compressed together from the skin non-contacting side toward the skin contacting side.

12. The absorbent article according to claim 1, further comprising another compressed portion adjacent to the break portion on the skin contacting side, and formed in a concave shape projecting toward the skin non-contacting side by compression from the skin contacting side toward the skin non-contacting side.

13. The absorbent article according to claim 1, wherein the back sheet is corrugated and stretchable in a transverse direction of the absorbent article, and the back sheet includes convex and concave portions extending in a longitudinal direction perpendicular to the transverse direction.

14. The absorbent article according to claim 1, further comprising a space arranged between a central core portion of the absorbent core and the back sheet in a thickness direction of the absorbent article,
wherein the absorbent core further has two transversely opposite side portions which are folded respectively, and the space is arranged between the side portions in a transverse direction of the absorbent article.

15. The absorbent article according to claim 14, wherein
the central core portion is between the side portions in the transverse direction, and
a thickness of the central core portion is less than that of each of the side portions.

* * * * *